United States Patent [19]

Forkner et al.

[11] Patent Number: 5,630,788
[45] Date of Patent: May 20, 1997

[54] ENDOSCOPE WITH CURVED END IMAGE GUIDE

[75] Inventors: John F. Forkner, South Laguna; Gary M. Woker, Escondido, both of Calif.

[73] Assignee: Imagyn Medical, Inc., Laguna Niguel, Calif.

[21] Appl. No.: 289,941

[22] Filed: Aug. 12, 1994

[51] Int. Cl.$^6$ .................... A61B 1/00; G02B 6/06
[52] U.S. Cl. .................... 600/182; 600/129; 600/176; 600/162; 385/117; 385/119
[58] Field of Search .................... 600/182, 176, 600/167, 177, 129; 385/33, 34, 35, 119, 117, 116

[56] References Cited

U.S. PATENT DOCUMENTS

| | | |
|---|---|---|
| 3,666,347 | 5/1972 | Kitano et al. . |
| 4,101,196 | 7/1978 | Imai . |
| 4,290,667 | 9/1981 | Chown .................... 385/34 |
| 4,457,590 | 7/1984 | Moore . |
| 4,487,646 | 12/1984 | Murray et al. . |
| 4,529,267 | 7/1985 | Nishioka et al. . |
| 4,577,926 | 3/1986 | Dewey et al. . |
| 4,650,279 | 3/1987 | Magee . |
| 4,684,221 | 8/1987 | Takada . |
| 4,721,369 | 1/1988 | Hattori et al. . |
| 4,755,029 | 7/1988 | Okabe . |
| 4,762,120 | 8/1988 | Hussein .................... 128/6 |
| 4,772,105 | 9/1988 | Takada . |
| 4,867,521 | 9/1989 | Mallinson .................... 385/34 |
| 4,874,220 | 10/1989 | Yamagata . |
| 5,029,963 | 7/1991 | Naselli et al. .................... 385/119 |
| 5,125,064 | 6/1992 | Naselli et al. .................... 385/33 |
| 5,172,272 | 12/1992 | Aoki . |
| 5,279,280 | 1/1994 | Bacich et al. . |
| 5,299,272 | 3/1994 | Buchin .................... 385/119 |
| 5,311,611 | 5/1994 | Migliaccio .................... 385/33 |

FOREIGN PATENT DOCUMENTS

| | | | |
|---|---|---|---|
| 4824742 | of 1973 | Japan . | |
| 625180 | 9/1978 | U.S.S.R. | .................... 385/119 |
| 1663597 | 7/1991 | U.S.S.R. | .................... 385/119 |

OTHER PUBLICATIONS

Third European Conference on Optical Communication, Sep. 1977, "A Luneberg Lens for the Efficient Coupling of Laser Diode and a Graded–Index Fiber", pp. 176–178.

*Primary Examiner*—Richard J. Apley
*Assistant Examiner*—John P. Leubecker
*Attorney, Agent, or Firm*—Donald E. Stout

[57] ABSTRACT

An endoscope comprising an elongated endoscope body having a distal end, an objective carried by the endoscope body adjacent the distal end and an elongated fiberoptic image guide in the endoscope body for transmitting an image proximally. The objective has a curved proximal surface and the image guide has a curved distal end surface which has a shape which generally conforms to the shape of the curved proximal surface of the objective. These surfaces are in close proximity to provide an interface and an index matching medium is in the interface. The objective provides a curved image plane substantially at the interface and the image plane has a shape which generally conforms to the shape of the curved proximal surface of the objective.

18 Claims, 3 Drawing Sheets

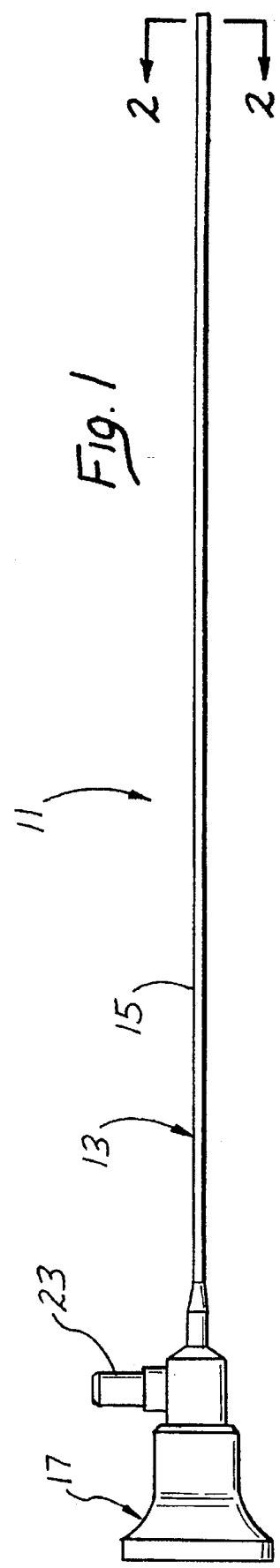
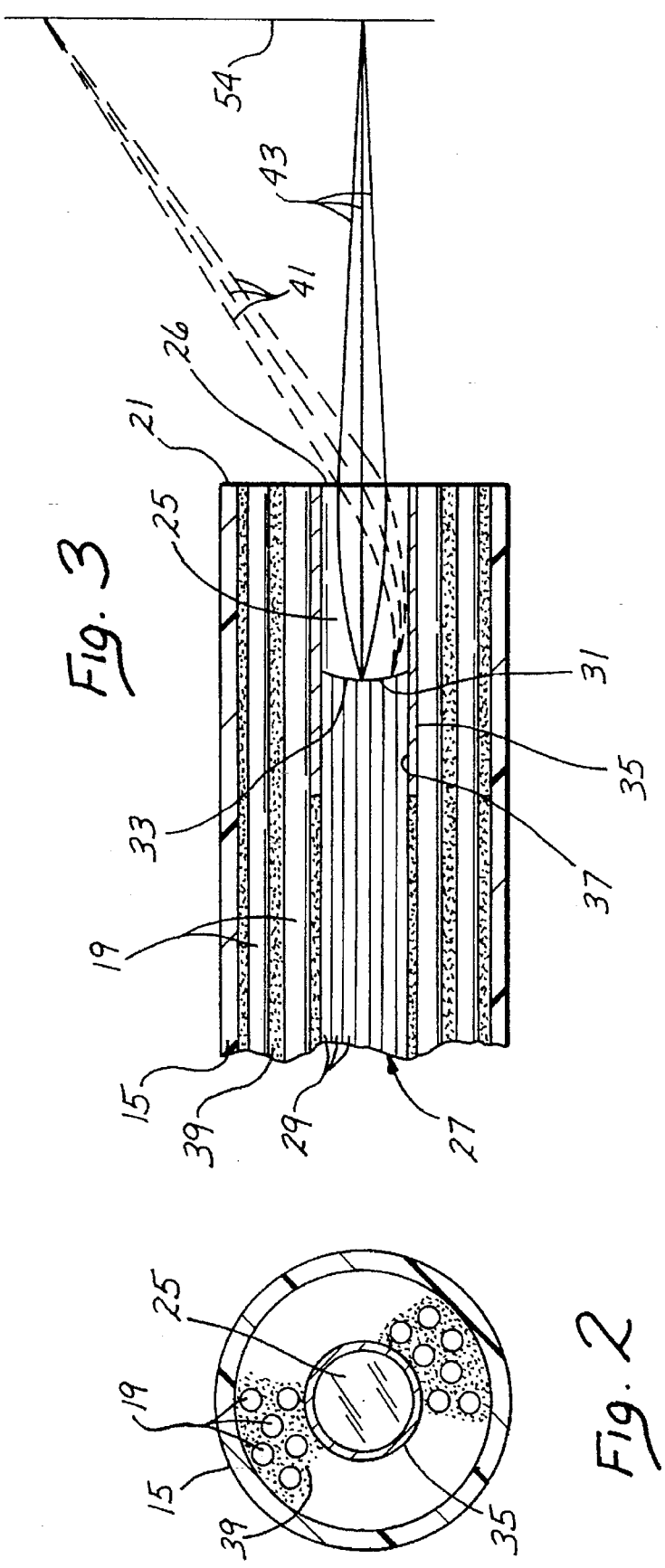
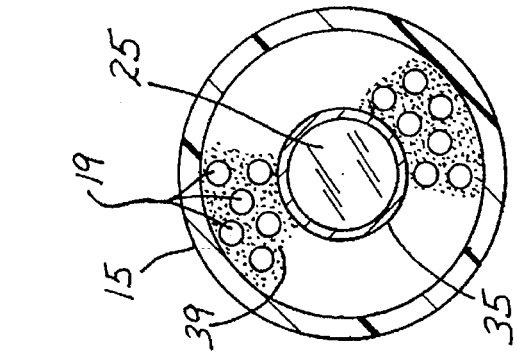

ENDOSCOPE WITH CURVED END IMAGE GUIDE

BACKGROUND OF THE INVENTION

Endoscopes are commonly used to view the interior passage of an object. Endoscopes have industrial applications wherein the endoscope is used to view a passage within, for example, a piece of equipment. Endoscopes also have medical applications wherein the endoscope is used to view a passage within the body of a patient.

An endoscope typically includes an endoscope body and optical components carried by the endoscope body to enable viewing of the passage distally of the distal end of the endoscope body. The optical components may also include illumination optics for illuminating the field of view, and such illumination optics may comprise optical fibers carried by the endoscope body.

The optical components also include the optics necessary to transmit or relay an image proximally and to provide the image to an eyepiece for direct visualization or to a camera which enables viewing of the scene on a T.V. monitor. These latter optics may include an objective for providing an image plane, eyepiece optics adjacent the proximal end of the endoscope body and an elongated fiberoptic image guide in the endoscope body for transmitting the image proximally to the eyepiece optics.

One problem with endoscopes of the type that includes an image guide is the field curvature introduced by the objective. It is often desirable for the objective to provide a relatively wide field of view, and this, in turn, tends to create field curvature. Consequently, the image plane formed by the objective is curved, and if the curved image plane is not properly accommodated, the image guide transmits an image that is partly out of focus to the eyepiece optics.

In an attempt to solve this problem, Yamagata U.S. Pat. No. 4,874,220 discloses an endoscope which provides a curved image plane spaced from the objective and a curved end surface on the image guide. The curvature of the end surface of the image guide substantially conforms to the curved image plane of the objective and is substantially located at the image plane. This is done for the purpose of attempting to form an image on the curved end surface of the image guide with all points of the image in focus. However, the refraction which occurs at the air-optical fiber interface tends to create dark regions in the image. Specifically, this tends to occur at locations where the end faces of the individual optical fibers of the image guide are at an angle with respect to the light rays which they receive.

Kitano et al U.S. Pat. No. 3,666,347 discloses an optical system having optical fibers which are curved to present end faces which are essentially normal to a curved image plane. Although this tends to reduce the problem of dark spots referred to above, curving the optical fibers in this fashion increases the cost and complexity of the structure. Published Japanese Patent Application No. 48(1973)-24742 also discloses an image guide with a curved end surface for accommodating a curved image plane. However, the image guide is spaced from the objective lens by a gap and in one embodiment the optical fibers are curved in the manner described above in connection with Kitano et al thereby introducing similar cost and complexity problems.

SUMMARY OF THE INVENTION

This invention solves the problems noted above. With the endoscope of this invention, the image provided to the eyepiece optics is in focus and does not have the dark regions discussed above. This is accomplished without the cost and complexity of curving the fibers and orienting the end faces of the fibers to be normal to the curved image plane.

The invention is applicable to an endoscope which includes an endoscope body having a distal end, illumination optics carried by the endoscope body for transmitting illumination distally in the endoscope body and an elongated fiberoptic image guide in the endoscope body for transmitting an image proximally. The objective provides a curved image plane. However, with this invention the curved image plane is provided substantially at the proximal surface of the objective rather than at a location spaced significantly from this proximal surface. Moreover, the curved proximal surface of the objective has a shape which generally conforms to the shape of the image plane.

The image guide has a curved distal end surface which has a shape which generally conforms to the shape of the curved proximal surface of the objective. The curved distal end face is in close proximity to the curved proximal surface of the objective to provide an interface. An index matching medium is in the interface and contacts the curved surfaces to reduce refraction at the interface. Consequently, the objective, the index matching medium and the image guide tend to act optically as a single optical element and the dark regions in the image discussed above do not tend to occur. This is accomplished without the need and the accompanying cost and complexity of curving the optical fibers of the image guide. In fact, with this invention the optical fibers which terminate at the interface are preferably substantially parallel at the interface.

The index matching medium need not be a perfect match between the indices of refraction of the objective and the image guide because any medium with an index of refraction of greater than one and not substantially above the index of refraction of the objective and the image guide would be an improvement over an air gap. For example, the index matching medium may have an index of refraction of between about 1.4 and 1.8 with an index between 1.45 and 1.7 being preferred. Although the index matching medium does not need to be an adhesive, preferably it is an optical adhesive which adheres the curved proximal surface of the objective to the curved distal end surface of the fiberoptic image guide and which holds these curved surfaces in intimate contact. The index matching medium and hence the interface are preferably very thin and may be for example no more than about 0.002 inch thick.

To further assure that the curved surfaces are in the desired intimate contact at the interface, a mechanical attachment such as a bushing having a passage may be employed with the passage receiving at least portions of the objective and the image guide. The bushing is preferably adhered to both the objective and the image guide.

Each of at least some of the optical fibers of the image guide terminate in an end face at the curved distal end surface. Preferably, each of these end faces generally conforms to a confronting region of the curved proximal surface of the objective. Some of these end faces, most notably those near the periphery of the image guide, form acute angle with a longitudinal axis of the associated optical fiber. Although the index matching medium is preferably between and in intimate contact with the entire confronting surfaces of the objective and image guide, to prevent the image from having a darkened periphery it is especially important that the index matching medium be between these end faces at the periphery and the associated confronting region of the objective.

The objective can be any optical element or group of optical elements which provide the desired image plane. For those applications in which low cost and simplicity are of paramount importance, the objective preferably includes a gradient index (GRIN) rod or lens. On the other hand, for those applications which can stand a higher cost, some optical improvement can be obtained with an objective which includes a plurality of refractive optical elements.

The eyepiece optics may also introduce field curvature into the system. Although this field curvature can be eliminated, it is generally more costly to provide eyepiece optics which do not exhibit field curvature. The features of this invention are also applicable to dealing with the field curvature introduced by the eyepiece optics.

To accomplish this, the image guide has a curved proximal end surface and the eyepiece optics have a curved distal surface with a shape which generally conforms to the shape of the curved proximal end surface of the image guide. These curved surfaces are in close proximity or in substantial engagement to provide a proximal interface. An index matching medium is provided in the proximal interface and it contacts the curved surfaces to reduce refraction at the proximal interface. The eyepiece optics provide a curved object plane substantially at the proximal interface and the object plane has a shape which generally conforms to the shape of the curved proximal end surface of the image guide.

Generally, the system adjacent the proximal end of the image guide functions similarly, but in a reverse mode, to the system at the distal end of the image guide. Thus, distally a flat object is projected on to a curved image plane and proximally a curved object is projected to a flat image plane. In either case, the advantages of the curved confronting surfaces and the index matching medium are very similar.

The invention, together with additional features and advantages thereof may best be understood by reference to the following description taken in connection with the accompanying illustrative drawings.

BRIEF DESCRIPTION OF THE DRAWINGS

FIG. 1 is a side elevational view of an endoscope constructed in accordance with the teachings of this invention.

FIG. 2 is an enlarged sectional view taken generally along line 2—2 of FIG. 1.

FIG. 3 is an enlarged, fragmentary, axial sectional view through a distal region of the endoscope and illustrating rays from an object being directed by a GRIN objective to a curved image plane.

DESCRIPTION OF THE PREFERRED EMBODIMENT

Figure 4:
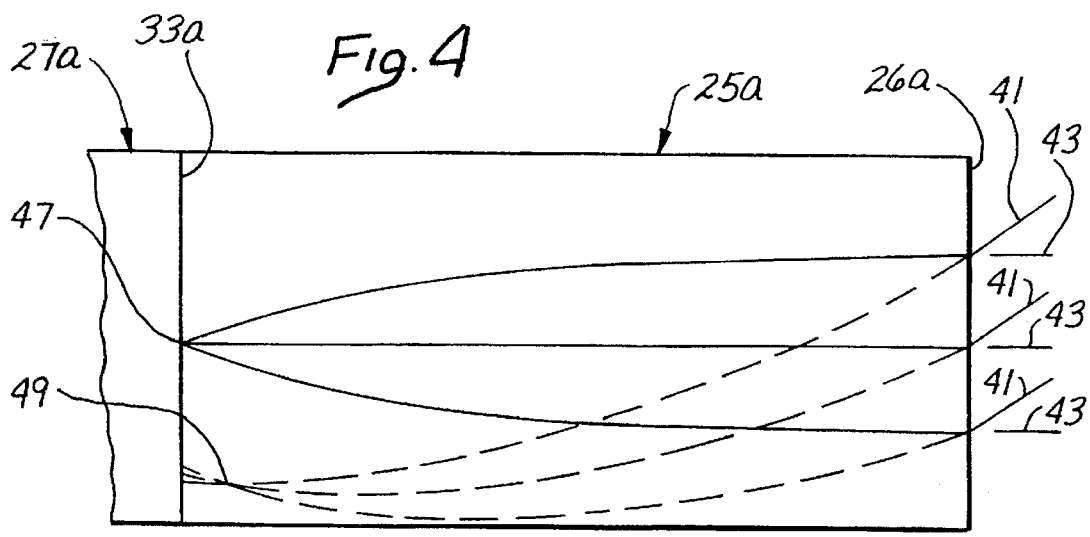
FIG. 4 is a schematic view showing how the field curvature of the GRIN objective provides a curved image plane which would create out of focus regions if an image guide with a flat end face were utilized.

FIG. 1 shows an endoscope 11 which generally comprises an endoscope body 13 and various optical components described below. The endoscope body 13 includes an elongated, tubular cylindrical sheath 15 and an eyepiece housing 17 attached to the sheath. Although the sheath 15 may be flexible or rigid, in this embodiment, the sheath 15 is rigid and is constructed of a rigid polymeric material or a suitable metal, such as stainless steel.

The sheath 15 is suitably attached to the eyepiece housing 17 in any suitable conventional manner. Although the features of this invention are applicable to endoscopes for industrial uses, in the illustrated embodiment of the invention, the endoscope is adapted for medical use such as laparoscopy or arthroscopy.

The endoscope 11 includes illumination optics in the form of illumination optical fibers 19 which extend from a distal end 21 of the endoscope body 13 through the sheath and a light cable connector 23 (FIGS. 1 and 7) of the eyepiece housing 17. The connector 23 is adapted to be coupled a source of illumination (not shown) so that light can be transmitted by the optical fibers 19 to the distal end 21 of the endoscope body 13 to illuminate the field of view.

Figure 7:
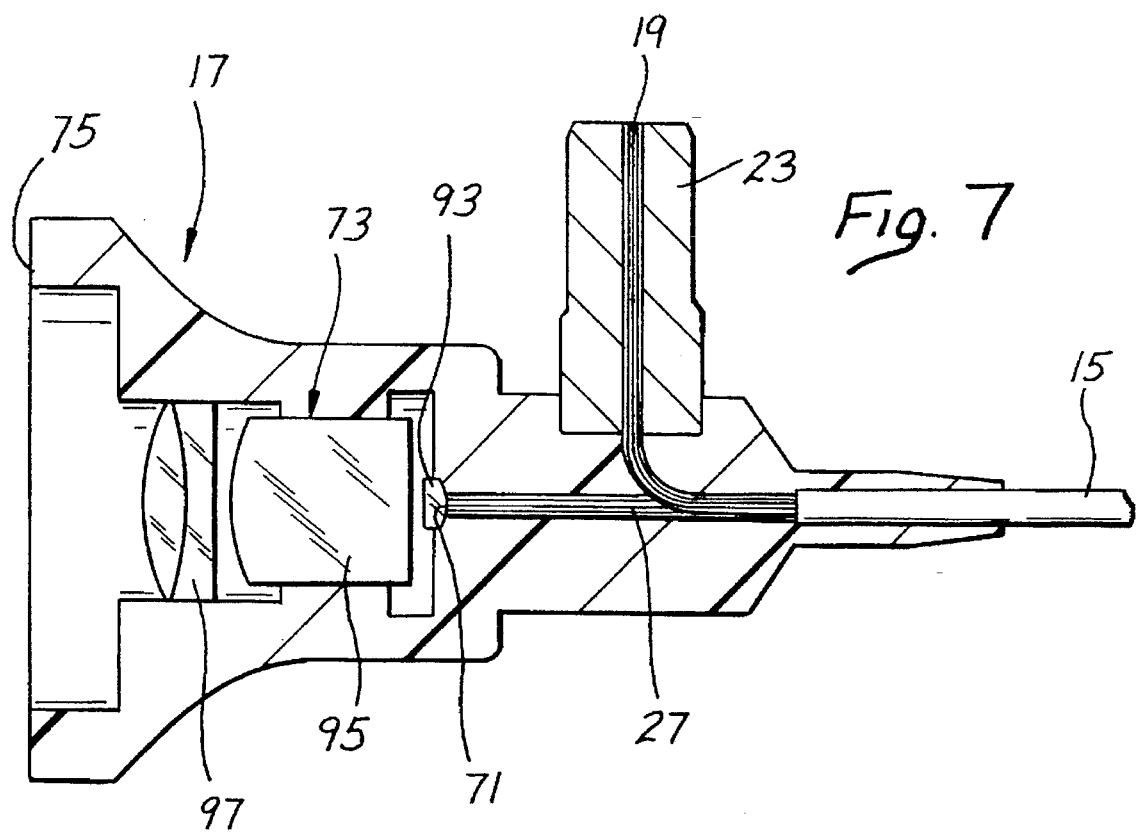
FIG. 7 is an axial sectional view through a proximal region of the endoscope.

The optical components also include an objective 25 (FIGS. 2 and 3) which has a distal end 26 and which is carried by the endoscope body 13 adjacent the distal end 21 and an elongated fiberoptic image guide 27 in the endoscope body for transmitting an image proximally. The image guide 27 extends completely through the sheath 15 and terminates in the eyepiece housing 17 (FIG. 7).

Figure 5:
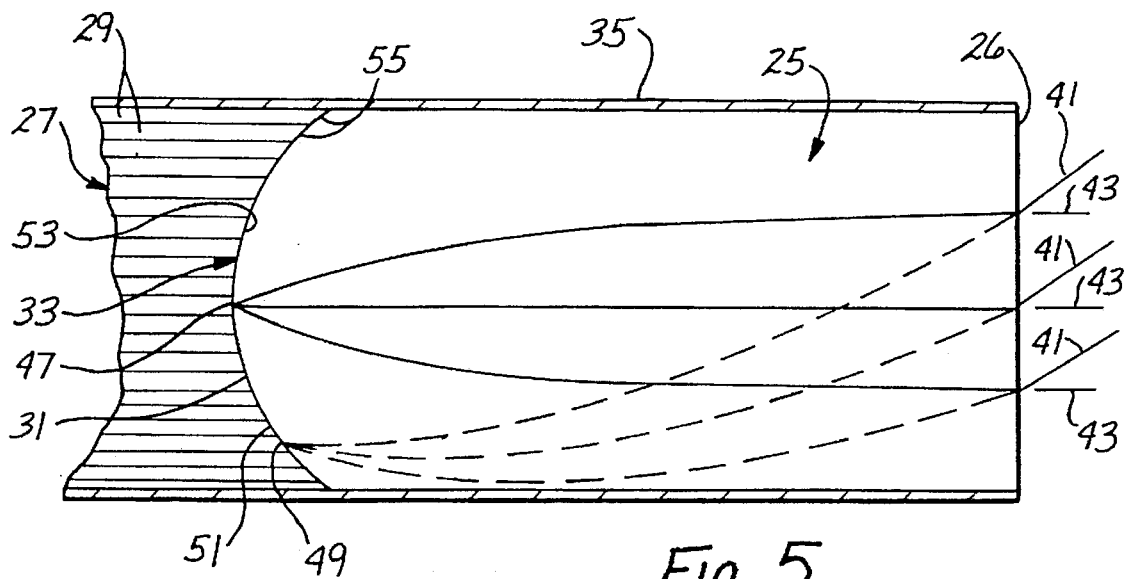
FIG. 5 is a schematic side elevational view partially in section of the GRIN objective and distal regions of the image guide of this invention.
Figure 6:
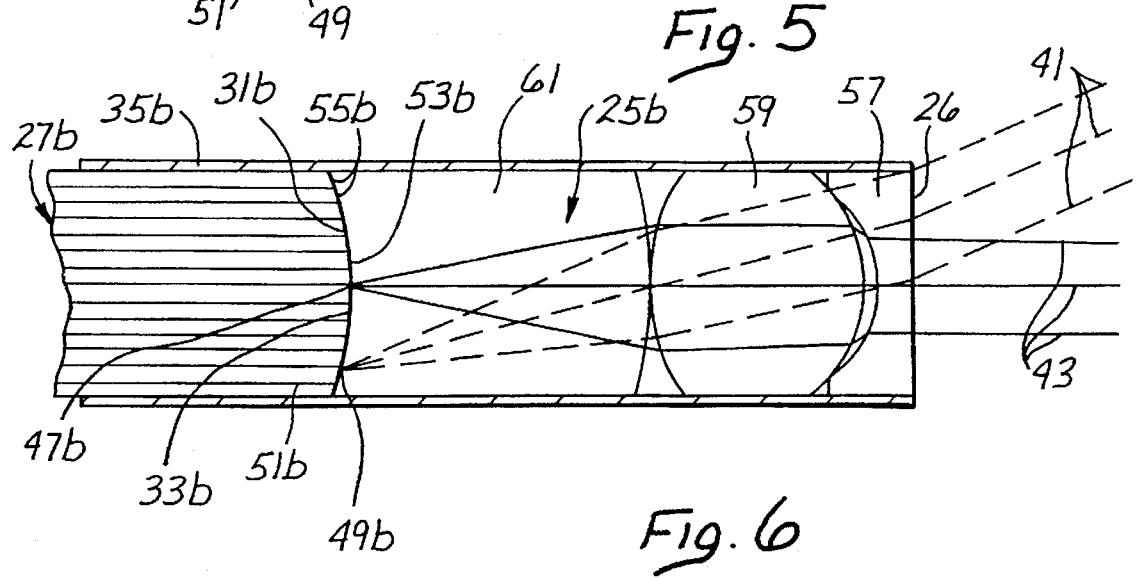
FIG. 6 is a view similar to FIG. 5 illustrating an objective which includes multiple refracting elements rather than a GRIN rod.

The image guide 27 comprises a coherent bundle of optical fibers 29 which are shown somewhat schematically in FIGS. 3, 5 and 6. Each of the fibers 29 is capable of transmitting or relaying a portion or pixel of an image such that the combined output of the image guide is an image.

An index matching medium in the form of an index matching adhesive or optical adhesive 31 is employed at an interface 33 between the objective 25 and the image guide 27 to adhere the objective to the image guide. To further mount these two components, a bushing 35 having a passage 37 receives the objective 25 and a distal portion of the image guide 27. The objective 25 and the distal portion of the image guide 27 are coupled to the bushing by a suitable adhesive.

Although various different orientations may be employed, in the embodiment illustrated, the bushing 35 is generally coaxial with the sheath 15 (FIG. 2) and the illumination optical fibers 19 are arranged in an annulus around the bushing. An adhesive, such as epoxy 39, joins the illumination optical fibers 19 together at the proximal and distal ends of the fibers.

The optical features of this invention can best be understood by considering FIG. 4 which shows a GRIN rod objective 25a and an image guide 27a neither of which is constructed in accordance with this invention. FIG. 4 shows schematically parallel rays 41 and parallel rays 43 similar to rays emanating from an object a infinity which strike the distal surface 26a of the objective 25a in two different directions. The parallel rays 43 are directed to a focus 47 and the parallel rays 41 are directed to a focus 49. The image guide 27a engages the objective 25a at an interface 33a. As shown in FIG. 4, the focus 47 is substantially at the interface 33a; however, the focus 49 is displaced proximally from the interface 33a. Consequently, the rays 41 as received by the image guide 27a, and any other rays which are focused out of the flat plane of the interface 33a, will be out of focus as received by the image guide 27a. Thus, a partly out-of-focus image will be transmitted by the image guide 27a.

As shown in FIG. 5, the objective 25 of this invention has a curved proximal surface 51 and the image guide has a curved distal end surface 53 with these two curved surfaces being in substantial engagement and substantially conforming to each other in shape. In this embodiment the surfaces 51 and 53 are curved in two planes and are generally spherical. However, the surfaces 51 and 53 may be of an aspherical shape. As shown in FIG. 5, the focal points 47 and 49 for parallel rays 43 and 41, respectively, from an object 54 (FIG. 3) are substantially at the interface 33 and may lie on the curved proximal surface 51. In fact, the objective 25 provides a curved image plane substantially at the interface 33. The image plane has a shape which substantially conforms to the shape of the curved proximal surface of the objective and in this embodiment is substantially spherical. Consequently, all points of the image transmitted by the image guide 27 are in focus. In FIG. 3 the rays 41 do not appear parallel to each other and the same is true for the rays 43. This is because the object 54 is not at infinity and because FIG. 3 is of necessity out of scale in that the distance from the distal end 21 to the object 54 is many times the diameter of the objective 25. For objects closer than infinity, the nonparallel rays will still form a curved image plane.

In this embodiment, the objective 25 is in the form of a GRIN rod. The objective 25 may have a refractive index of about 1.6 to about 1.7 and the optical fibers 29 of the image guide 27 may have a refractive index of about 1.53 to about 1.65. By way of example, the index matching adhesive 31 may have a refractive index of about 1.45 to about 1.7 to thereby greatly reduce refraction at the interface 33 and to reduce the likelihood that the image transmitted by the image guide 27 will have dark peripheral regions. The index matching adhesive 31 is very thin and may be of the order of no greater than 0.002 inch with a thickness of no greater than about 0.001 inch being preferred. Consequently, an image plane which is substantially at the very thin interface 33 is within the depth of focus of the optics.

As shown in FIG. 5, each of the optical fibers 29 terminates in an end face 55 at the curved distal end surface 53. As shown in FIGS. 3 and 5, the optical fibers 29 at the interface 33 are substantially parallel, and moreover the optical fibers 29 may be substantially parallel throughout the full length of the image guide 27.

Because the curved distal end surface 53 conforms in shape to the curved proximal surface 51, each of the end faces 55 generally conforms in shape to a confronting region of the curved proximal surface 51 of the objective 25. Those end faces 55 near the periphery of the image guide 27 form acute angle with the longitudinal axis of the associated fiber 29. If an air gap existed at the interface 33 between an angled end face 55 near the periphery of the image guide 27 and the objective 25, the periphery of the image would appear dark at the proximal end of the image guide 27. This is due to refraction at the periphery of the interface 33 causing the light to deviate outside the acceptance angle of the individual fibers 29. Consequently, it is particularly important to have the index matching adhesive 35 between such angled end faces 55 and the associated confronting region of the objective 25. In this embodiment, the index matching adhesive 31 covers the entire interface 33 between the curved proximal surface 51 and the curved distal end surface 53.

In the construction of FIG. 5, a GRIN rod is used for the objective 25 and it provides a convex image plane as viewed in either axial or radial cross section. In addition, in the form shown in FIG. 5, the image plane forms a portion of a sphere.

FIG. 6 illustrates that the objective 25b may comprise a plurality of refractive optical elements such as lenses 57, 59 and 61 and that the image plane at the interface 33b may be concave. Portions of the embodiment of FIG. 6 corresponding to portions of the embodiment of FIG. 5 are designated by corresponding reference numerals followed by the letter "b". The embodiment of FIG. 6 is identical to the embodiment of FIG. 5 in all respects not shown or described herein.

The objective 25b may of conventional construction, and in that regard the distal lens 57 may be a plano convex lens, the intermediate lens 59 may be a double convex lens and the proximal lens 61 may be concavo-convex. The lenses 57, 59 and 61 are suitably adhered within the bushing 35b. As shown in FIG. 6 the objective 25b focuses the rays 41 and 43 at the focuses 49b and 47b, respectively, as described above in connection with the FIG. 5. The proximal lens 61 has a curved proximal surface 51b on which all of the focal points or focuses from all of the rays incident upon the distal lens 57 fall such that the concave image plane lies substantially along and substantially conforms to the shape of the curved proximal surface 51b. The image guide 27b has a curved distal end surface 53b in close proximity to the curved proximal surface 51b to provide the interface 33b and shape of these curved surfaces are substantially in conformity. Thus, the embodiment of FIG. 6 is identical to the embodiment of FIG. 5 except for the multiple optical component objective 25b, the shape of the surfaces 51b and 53b and the shape of the interface 33b.

The image formed at the image plane along the interface 33 is transmitted by the image guide 27 proximally to a proximal end surface 71 (FIG. 7 and 8) of the image guide. Eyepiece optics 73 (FIGS. 7 and 8) are carried by the eyepiece housing 17. The proximal end surface 71 of the image guide 27 forms an object plane for the eyepiece optics 73, and the eyepiece optics 73 transmit an image of the object at the object plane proximally to an eye cup 75 for direct viewing by the user of the endoscope 11. Alternatively, the eyepiece optics 73 may direct the image of the object to suitable camera for enabling the image to be viewed on a T.V. monitor.

The eyepiece optics 73 in this embodiment also introduce field curvature into the optical system, and this field curvature is accommodated by this invention in much the same manner as described above for the field curvature introduced by the objective 25.

Optical systems can be analyzed by considering rays of illumination moving through the system in either direction. For purposes of understanding the field of curvature introduced by the eyepiece optics 73, it is convenient to consider parallel rays 77 and a second group of parallel rays 79 being transmitted through the eyepiece optics 73 in a reverse direction, from left to right as viewed in FIG. 8. From FIG. 8 it can be seen that the eyepiece optics bring the parallel rays 77 at a focus 81 and bring the parallel rays 79 at a focus 83. The focuses 81 and 83 along with similar focuses from other rays (not shown) define a concavely curved object plane which is substantially at a proximal interface 85 between the proximal end surface 71 and a curved distal surface 87 of the eyepiece optics. The proximal end surface 71 of the image guide is curved concavely and substantially conforms to the shape of the curved distal surface 87. In this embodiment the surfaces 71 and 87 and the object plane are curved in two planes and are part spherical.

An index matching medium in the form of an index matching adhesive 89 fully covers the proximal interface 85 and contacts the curved surfaces 71 and 87 to reduce refraction at the proximal interface. All other factors regarding the thickness and index of refraction of the index matching adhesive discussed above for the index matching adhesive 31 are applicable to the index matching adhesive 89, and like the surfaces 51 and 52, the surface 71 and 87 are in close proximity and preferably in substantial contact being spaced only by the very thin layer of the index matching adhesive 89 which holds them together. Thus, all of the teachings set forth above with respect to the surfaces 51 and 53, the interface 33 and the adhesive 31 are equally applicable to the surfaces 71 and 87, the adhesive 89 and the proximal interface 85.

Figure 8:
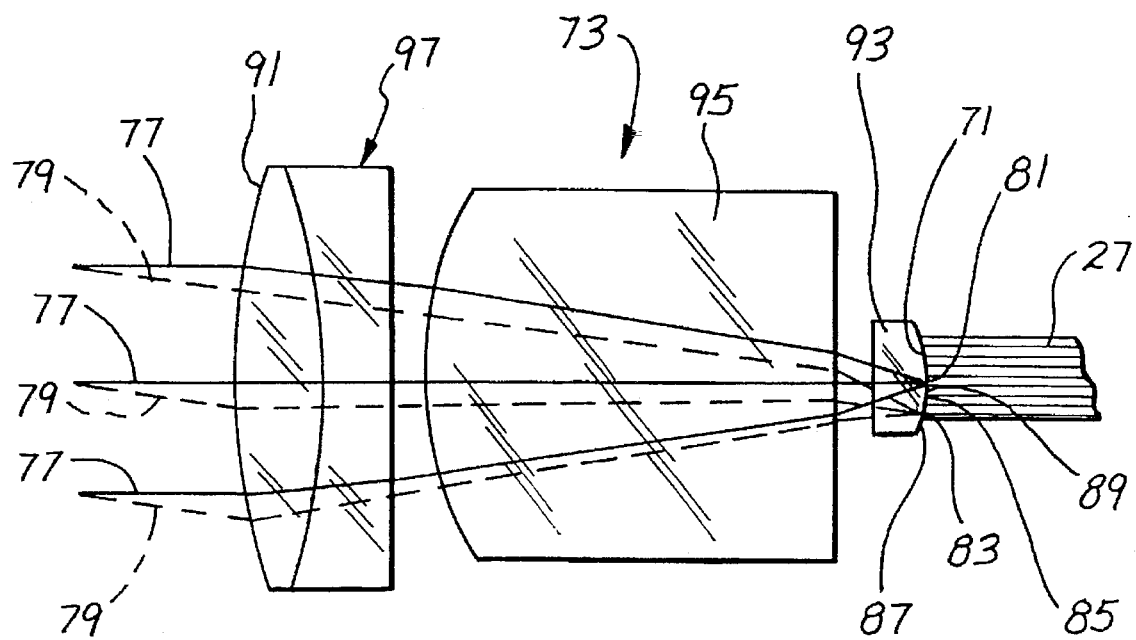
FIG. 8 is a ray tracing for the eyepiece optics.

From FIG. 8 and the discussion above, it can be seen that the eyepiece optics can transmit an image of an object at the curved object plane which lies substantially along the proximal interface 85. Thus, the rays emanating from each point of the object plane, e.g. the focuses 81 and 83, are parallel as they leave a proximal surface 91 of the eyepiece optics 73. Accordingly, the eyepiece optics 73 converts the curved object at the curved object plane to a flat image.

The features of this invention applicable to the eyepiece optics 73 are applicable to eyepiece optics of virtually any construction so long as the eyepiece optics introduce field curvature and the particular eyepiece optics shown FIGS. 7 and 8 are purely illustrative. In FIGS. 7 and 8, the eyepiece optics 73 include a proximal plano convex lens 93 which has its convex surface forming the curved distal surface 87 and a plano convex intermediate lens 95. The eyepiece optics 73 also includes an doublet 97 which provides the proximal surface 91. The lenses 93, 95 and 97 may be mounted in the eyepiece housing 17 in any suitable manner. For example, the lens 93 is adhered to the image guide 27 by the index matching adhesive 89 and the lenses 95 and 97 may be adhered to the eyepiece housing 17.

In use, the connector 23 is coupled to a source of illumination (not shown) and the sheath 15 is inserted into a passage that is to be examined. The passage may be in machinery or within a human or animal body. The objective 25 provides a curved image plane substantially at the curved interface 33 and the image guide 27 transmits the image at the curved image plane proximally to the curved object plane at the proximal interface 85. The eyepiece optics 73 transmits an image of the object at the curved object plane proximally for direct viewing.

Although exemplary embodiments of the invention have been shown and described, many changes, modifications and substitutions may be made by one having ordinary skill in the art without necessarily departing from the spirit and scope of this invention.

We claim:

1. An endoscope comprising:

an elongated endoscope body having a distal end;

an objective carried by the endoscope body adjacent said distal end, said objective including a gradient index rod having a curved proximal surface thereon;

an elongated fiberoptic image guide in the endoscope body for transmitting an image proximally, said image guide having a curved distal end surface which has a shape which generally conforms to the shape of the curved proximal surface of the gradient index rod, said curved distal end surface being substantially in contact with the curved proximal surface of the gradient index rod to provide a distal interface;

an index matching medium in the interface and contacting said curved surfaces to reduce refraction at the distal interface;

said gradient index rod providing a curved image plane substantially at said distal interface, said image plane having a shape which generally conforms to the shape of the curved proximal surface of the gradient index rod whereby the image guide can transmit an image at the image plane proximally;

said fiberoptic image guide further having a curved proximal end surface, the endoscope including eyepiece optics having a curved distal surface which has a shape generally conforming to the shape of the curved proximal and surface of the image guide, said curved distal surface of the eyepiece optics being in close proximity to the curved proximal end surface of the image guide to provide a proximal interface;

an index matching medium in the proximal interface and contacting said curved proximal surface of the image guide and said curved distal surface of the eyepiece optics to reduce refraction at the proximal interface, said eyepiece optics providing a curved object plane substantially at said proximal interface, said curved object plane having a shape which generally conforms to the shape of the curved proximal end surface of the image guide whereby the eyepiece optics can transmit an image of an object at the object plane.

2. An endoscope as defined in claim 1 wherein the index matching medium at the distal interface includes an optical adhesive for adhering the curved proximal surface of the gradient index rod to the curved distal end surface of the fiberoptic image guide.

3. An endoscope as defined in claim 1 wherein the index matching medium at the distal interface has a refractive index of between about 1.4 and about 1.8.

4. An endoscope as defined in claim 1 wherein the image guide includes optical fibers terminating at said distal interface, said optical fibers at said distal interface being substantially parallel.

5. An endoscope as defined in claim 4 wherein each of at least some of said fibers terminates in an end face at the curved distal end surface of the fiberoptic image guide, said end face generally conforming to a confronting region of the curved proximal surface of the gradient index rod and forming an acute angle with a longitudinal axis of such fiber, and the index matching medium at the distal interface is between each of said optical fiber end faces and the associated confronting region.

6. An endoscope as defined in claim 1 including a bushing having a passage, said passage receiving at least portions of the objective and the image guide.

7. An endoscope as defined in claim 1 wherein the image plane is substantially spherical.

8. An endoscope comprising:

an elongated endoscope body having a distal end;

an objective carried by the endoscope body adjacent said distal end, said objective having a curved proximal surface;

an elongated fiberoptic image guide in the endoscope body for transmitting an image proximally, said image guide having a convex curved distal end surface which has a shape which generally conforms to the shape of the curved proximal surface of the objective, said curved distal end surface being substantially in contact with the curved proximal surface of the objective to provide an interface;

said objective providing a curved image plane substantially at said interface, said image plane having a shape which generally conforms to the shape of the curved proximal surface of the objective whereby the image guide can transmit an image at the image plane proximally; and the image guide including optical fibers terminating at said interface, said optical fibers at said interface being substantially parallel.

9. An endoscope as defined in claim 8 wherein the objective includes a gradient index rod having said curved proximal surface thereon.

10. An endoscope as defined in claim 8 wherein the index matching adhesive has an index of refraction of between about 1.45 and about 1.7.

11. An endoscope as defined in claim 8 wherein each of at least some of said fibers terminates in an end face at said curved distal end surface, said end face generally conforms to a confronting region of said curved proximal surface of the objective and forms an acute angle with a longitudinal axis of such fiber and the index matching adhesive is between each of said end faces and the associated confronting region.

12. An endoscope as defined in claim 8 wherein said interface is no more than about 0.002 inch thick.

13. An endoscope as defined in claim 8 including a bushing having a passage, said passage receiving at least portions of the objective and the image guide.

14. An endoscope as defined in claim 11 including illumination optics carried by the endoscope body for transmitting illumination distally in the endoscope body.

15. An endoscope as defined in claim 8, wherein the objective includes a plurality of refractive optical elements.

16. An endoscope as defined in claim 15, wherein each of said optical elements is in physical contact with another one of said optical elements.

17. An endoscope comprising:

an elongated endoscope body having a distal end;

an objective carried by the endoscope body adjacent said distal end, said objective having an image plane;

an elongated fiberoptic image guide in the endoscope body for transmitting an image from the image plane proximally, said image guide having a curved proximal end surface;

eyepiece optics having a curved distal surface which has a shape which generally conforms to the shape of the curved proximal end surface of the image guide, said curved distal surface of the eyepiece optics being in close proximity to the curved proximal end surface of the image guide to provide a proximal interface;

an index matching medium in the proximal interface and contacting said curved surfaces to reduce refraction at the proximal interface; and said eyepiece optics providing a curved object plane substantially at said proximal interface, said curved object plane having a shape which generally conforms to the shape of the curved proximal end surface of the image guide whereby the eyepiece optics can transmit an image of an object at the object plane.

18. An endoscope as defined in claim 17 wherein the index matching medium includes an optical adhesive for adhering said curved proximal end surface of the image guide to said curved distal surface of the eyepiece optics.

* * * * *